United States Patent
Burdulis

(10) Patent No.: US 9,427,570 B2
(45) Date of Patent: Aug. 30, 2016

(54) EXPANDABLE STIMULATION LEADS AND METHODS OF USE

(75) Inventor: Albert G. Burdulis, San Francisco, CA (US)

(73) Assignee: St. Jude Medical Luxembourg Holdings SMI S.A.R.L. ("SJM LUX SMI"), Luxembourg (LU)

( * ) Notice: Subject to any disclaimer, the term of this patent is extended or adjusted under 35 U.S.C. 154(b) by 878 days.

(21) Appl. No.: 11/952,065

(22) Filed: Dec. 6, 2007

(65) Prior Publication Data

US 2008/0140153 A1    Jun. 12, 2008

Related U.S. Application Data

(60) Provisional application No. 60/873,465, filed on Dec. 6, 2006.

(51) Int. Cl.
*A61N 1/05* (2006.01)

(52) U.S. Cl.
CPC .................. *A61N 1/0551* (2013.01)

(58) Field of Classification Search
CPC ................................. A61N 1/0551
USPC ................................. 607/46, 117
See application file for complete search history.

(56) References Cited

U.S. PATENT DOCUMENTS

| | | |
|---|---|---|
| 525,891 A | 9/1894 | Fricke |
| 3,724,467 A | 4/1973 | Avery et al. |
| 3,845,770 A | 11/1974 | Theeuwes et al. |
| 3,916,899 A | 11/1975 | Theeuwes et al. |
| 4,141,367 A | 2/1979 | Ferreira |
| 4,232,679 A | 11/1980 | Schulman |
| 4,298,003 A | 11/1981 | Theeuwes et al. |
| 4,313,448 A | 2/1982 | Stokes |
| 4,374,527 A | 2/1983 | Iversen |
| 4,479,491 A | 10/1984 | Martin |
| 4,549,556 A | 10/1985 | Tarjan et al. |
| 4,573,481 A | 3/1986 | Bullara |

(Continued)

FOREIGN PATENT DOCUMENTS

| | | |
|---|---|---|
| CN | 2401143 Y | 10/2000 |
| CN | 101594907 A | 12/2009 |

(Continued)

OTHER PUBLICATIONS

Abdulla et al.; Axotomy- and autotomy-induced changes in the excitability of rat dorsal root ganglion neurons: J Neurophysiol; 85(2); pp. 630-643; Feb. 2001.

(Continued)

*Primary Examiner* — Eric D. Bertram

(57) ABSTRACT

Devices, systems and methods are provided for stimulating a target tissue, particularly a dorsal root ganglion. The devices and systems have one or more electrodes, wherein the electrodes are positionable in disperse locations within the specific target area. In some embodiments, the position of at least some of the electrodes is adjustable and optionally independently positionable. Some or all of the electrodes may be used to stimulate the desired tissue, such as to stimulate a specific portion of the target area. Or, the one or more electrodes that fall near the target tissue may be used to stimulate the tissue while the other electrodes are not used. When stimulating the dorsal root ganglion, sensory pain signals are blocked providing relief to the patient.

12 Claims, 8 Drawing Sheets

(56) References Cited

U.S. PATENT DOCUMENTS

| | | |
|---|---|---|
| 4,577,642 A | 3/1986 | Stokes |
| 4,590,946 A | 5/1986 | Loeb |
| 4,607,639 A | 8/1986 | Tanagho et al. |
| 4,739,764 A | 4/1988 | Lue et al. |
| 4,786,155 A | 11/1988 | Fantone et al. |
| 4,803,988 A | 2/1989 | Thomson |
| 4,920,979 A | 5/1990 | Bullara |
| 4,940,065 A | 7/1990 | Tanagho et al. |
| 4,950,270 A | 8/1990 | Bowman et al. |
| 4,976,711 A | 12/1990 | Parins et al. |
| 5,135,525 A | 8/1992 | Biscoping et al. |
| 5,270,099 A | 12/1993 | Kamiyama et al. |
| 5,299,569 A | 4/1994 | Wernicke et al. |
| 5,344,438 A | 9/1994 | Testerman et al. |
| 5,358,514 A | 10/1994 | Schulman et al. |
| 5,370,644 A | 12/1994 | Langberg |
| 5,411,537 A | 5/1995 | Munshi et al. |
| 5,411,540 A | 5/1995 | Edell et al. |
| 5,417,719 A | 5/1995 | Hull et al. |
| 5,419,763 A | 5/1995 | Hildebrand |
| 5,458,626 A | 10/1995 | Krause |
| 5,489,294 A | 2/1996 | McVenes et al. |
| 5,505,201 A | 4/1996 | Grill et al. |
| 5,514,175 A | 5/1996 | Kim et al. |
| 5,584,835 A | 12/1996 | Greenfield |
| 5,634,462 A | 6/1997 | Tyler et al. |
| 5,643,330 A | 7/1997 | Holsheimer et al. |
| 5,702,429 A | 12/1997 | King |
| 5,711,316 A | 1/1998 | Elsberry et al. |
| 5,713,922 A | 2/1998 | King |
| 5,720,099 A | 2/1998 | Parker et al. |
| 5,733,322 A | 3/1998 | Starkebaum |
| 5,741,319 A | 4/1998 | Woloszko et al. |
| 5,755,750 A | 5/1998 | Petruska et al. |
| 5,776,170 A | 7/1998 | MacDonald et al. |
| 5,807,339 A | 9/1998 | Bostrom et al. |
| 5,824,021 A | 10/1998 | Rise |
| 5,865,843 A | 2/1999 | Baudino |
| 5,871,531 A | 2/1999 | Struble |
| 5,885,290 A | 3/1999 | Guerrero et al. |
| 5,938,690 A | 8/1999 | Law et al. |
| 5,948,007 A | 9/1999 | Starkebaum et al. |
| 5,957,965 A | 9/1999 | Moumane et al. |
| 5,983,141 A | 11/1999 | Sluijter et al. |
| 5,984,896 A | 11/1999 | Boyd |
| 6,002,964 A | 12/1999 | Feler et al. |
| 6,044,297 A | 3/2000 | Sheldon et al. |
| 6,045,532 A | 4/2000 | Eggers et al. |
| 6,051,017 A | 4/2000 | Loeb et al. |
| 6,104,957 A | 8/2000 | Alo et al. |
| 6,120,467 A | 9/2000 | Schallhorn |
| 6,161,048 A | 12/2000 | Sluijter et al. |
| 6,175,764 B1 | 1/2001 | Loeb et al. |
| 6,181,965 B1 | 1/2001 | Loeb et al. |
| 6,185,455 B1 | 2/2001 | Loeb et al. |
| 6,205,359 B1 | 3/2001 | Boveja |
| 6,208,902 B1 | 3/2001 | Boveja |
| 6,214,016 B1 | 4/2001 | Williams et al. |
| 6,259,952 B1 | 7/2001 | Sluijter et al. |
| 6,298,256 B1 * | 10/2001 | Meyer ............... 600/373 |
| 6,314,325 B1 | 11/2001 | Fitz |
| 6,319,241 B1 | 11/2001 | King et al. |
| 6,349,233 B1 | 2/2002 | Adams |
| 6,353,762 B1 * | 3/2002 | Baudino et al. ........ 607/45 |
| 6,356,786 B1 | 3/2002 | Rezai et al. |
| 6,360,750 B1 | 3/2002 | Gerber et al. |
| 6,366,814 B1 | 4/2002 | Boveja et al. |
| 6,393,325 B1 | 5/2002 | Mann et al. |
| 6,413,255 B1 | 7/2002 | Stern |
| 6,425,887 B1 | 7/2002 | McGuckin et al. |
| 6,438,423 B1 | 8/2002 | Rezai et al. |
| 6,440,090 B1 | 8/2002 | Schallhorn |
| 6,466,821 B1 | 10/2002 | Pianca et al. |
| 6,493,588 B1 | 12/2002 | Malaney et al. |
| 6,510,347 B2 | 1/2003 | Borkan |
| 6,512,958 B1 | 1/2003 | Swoyer et al. |
| 6,516,227 B1 | 2/2003 | Meadows et al. |
| 6,517,542 B1 | 2/2003 | Papay et al. |
| 6,522,926 B1 | 2/2003 | Kieval et al. |
| 6,535,767 B1 | 3/2003 | Kronberg |
| 6,582,441 B1 | 6/2003 | He et al. |
| 6,587,725 B1 | 7/2003 | Durand et al. |
| 1,605,094 A1 | 8/2003 | Mann et al. |
| 6,606,521 B2 | 8/2003 | Paspa et al. |
| 6,611,715 B1 | 8/2003 | Boveja |
| 6,625,496 B1 | 9/2003 | Ollivier |
| 6,638,276 B2 | 10/2003 | Sharkey et al. |
| 6,658,302 B1 | 12/2003 | Kuzma et al. |
| 6,714,822 B2 | 3/2004 | King et al. |
| 6,745,079 B2 * | 6/2004 | King ............... 607/117 |
| 6,748,276 B1 | 6/2004 | Daignault, Jr. et al. |
| 6,754,539 B1 | 6/2004 | Erickson et al. |
| 6,788,975 B1 | 9/2004 | Whitehurst et al. |
| 6,792,318 B2 | 9/2004 | Chitre et al. |
| 6,832,115 B2 | 12/2004 | Borkan |
| 6,835,194 B2 | 12/2004 | Johnson et al. |
| 6,839,588 B1 | 1/2005 | Rudy |
| 6,849,075 B2 | 2/2005 | Bertolero et al. |
| 6,862,479 B1 | 3/2005 | Whitehurst et al. |
| 6,871,099 B1 | 3/2005 | Whitehurst et al. |
| 6,873,342 B2 | 3/2005 | Perry et al. |
| 6,889,094 B1 | 5/2005 | Kuzma et al. |
| 6,901,287 B2 | 5/2005 | Davis et al. |
| 6,902,547 B2 | 6/2005 | Aves et al. |
| 6,909,917 B2 | 6/2005 | Woods et al. |
| 6,928,320 B2 | 8/2005 | King |
| 6,971,391 B1 | 12/2005 | Wang et al. |
| 6,978,180 B2 | 12/2005 | Tadlock |
| 7,047,082 B1 | 5/2006 | Schrom et al. |
| 7,096,070 B1 | 8/2006 | Jenkins et al. |
| 7,127,287 B2 | 10/2006 | Duncan et al. |
| 7,181,289 B2 | 2/2007 | Pflueger et al. |
| 7,333,857 B2 | 2/2008 | Campbell |
| 2001/0003799 A1 | 6/2001 | Boveja |
| 2001/0006967 A1 | 7/2001 | Crain et al. |
| 2002/0064841 A1 | 5/2002 | Klemic et al. |
| 2002/0077684 A1 * | 6/2002 | Clemens et al. ........ 607/116 |
| 2002/0087113 A1 | 7/2002 | Hartlaub |
| 2002/0099430 A1 | 7/2002 | Verness |
| 2002/0116030 A1 | 8/2002 | Rezai |
| 2002/0128694 A1 | 9/2002 | Holsheimer |
| 2002/0147486 A1 | 10/2002 | Soukup et al. |
| 2002/0198527 A1 | 12/2002 | Muckter |
| 2003/0018367 A1 | 1/2003 | Dilorenzo |
| 2003/0023241 A1 | 1/2003 | Drewry et al. |
| 2003/0045919 A1 | 3/2003 | Swoyer et al. |
| 2003/0069569 A1 | 4/2003 | Burdette et al. |
| 2003/0078633 A1 | 4/2003 | Firlik et al. |
| 2003/0088301 A1 | 5/2003 | King |
| 2003/0100933 A1 | 5/2003 | Ayal et al. |
| 2003/0114905 A1 | 6/2003 | Kuzma |
| 2003/0130577 A1 | 7/2003 | Purdy et al. |
| 2003/0144657 A1 | 7/2003 | Bowe et al. |
| 2003/0144709 A1 | 7/2003 | Zabara et al. |
| 2003/0181958 A1 | 9/2003 | Dobak, III |
| 2003/0187490 A1 | 10/2003 | Gliner |
| 2003/0195602 A1 | 10/2003 | Boling |
| 2003/0220677 A1 | 11/2003 | Doan et al. |
| 2004/0015202 A1 | 1/2004 | Chandler et al. |
| 2004/0019359 A1 | 1/2004 | Worley et al. |
| 2004/0019369 A1 | 1/2004 | Duncan et al. |
| 2004/0059404 A1 | 3/2004 | Bjorklund et al. |
| 2004/0116977 A1 | 6/2004 | Finch et al. |
| 2004/0122360 A1 * | 6/2004 | Waldhauser et al. ...... 604/95.04 |
| 2004/0122477 A1 | 6/2004 | Whitehurst et al. |
| 2004/0122497 A1 | 6/2004 | Zhang et al. |
| 2004/0122498 A1 | 6/2004 | Zhang et al. |
| 2004/0147992 A1 | 7/2004 | Bluger et al. |
| 2004/0172089 A1 | 9/2004 | Whitehurst et al. |
| 2004/0210290 A1 | 10/2004 | Omar-Pasha |
| 2004/0215286 A1 | 10/2004 | Stypulkowski |
| 2004/0230273 A1 | 11/2004 | Cates et al. |
| 2004/0230280 A1 | 11/2004 | Cates et al. |
| 2004/0243210 A1 | 12/2004 | Morgan et al. |

(56) References Cited

U.S. PATENT DOCUMENTS

| | | |
|---|---|---|
| 2005/0027338 A1 | 2/2005 | Hill |
| 2005/0033295 A1 | 2/2005 | Wisnewski |
| 2005/0033393 A1 | 2/2005 | Daglow |
| 2005/0038489 A1 | 2/2005 | Grill |
| 2005/0070982 A1 | 3/2005 | Heruth et al. |
| 2005/0080325 A1 | 4/2005 | Erickson |
| 2005/0090885 A1 | 4/2005 | Harris et al. |
| 2005/0096718 A1 | 5/2005 | Gerber et al. |
| 2005/0149154 A1 | 7/2005 | Cohen et al. |
| 2005/0154437 A1 | 7/2005 | Williams |
| 2005/0159799 A1 | 7/2005 | Daglow et al. |
| 2005/0203599 A1 | 9/2005 | Garabedian et al. |
| 2005/0222647 A1 | 10/2005 | Wahlstrand et al. |
| 2005/0251237 A1 | 11/2005 | Kuzma et al. |
| 2006/0004364 A1 | 1/2006 | Green et al. |
| 2006/0009820 A1 | 1/2006 | Royle |
| 2006/0041295 A1 | 2/2006 | Osypka |
| 2006/0052826 A1 | 3/2006 | Kim et al. |
| 2006/0052827 A1 | 3/2006 | Kim et al. |
| 2006/0052828 A1 | 3/2006 | Kim et al. |
| 2006/0052835 A1 | 3/2006 | Kim et al. |
| 2006/0052836 A1 | 3/2006 | Kim et al. |
| 2006/0052837 A1 | 3/2006 | Kim et al. |
| 2006/0052838 A1 | 3/2006 | Kim et al. |
| 2006/0052839 A1* | 3/2006 | Kim et al. .................... 607/48 |
| 2006/0052856 A1 | 3/2006 | Kim et al. |
| 2006/0064150 A1 | 3/2006 | Heist et al. |
| 2006/0089609 A1 | 4/2006 | Bleich et al. |
| 2006/0089696 A1 | 4/2006 | Olsen et al. |
| 2006/0094976 A1 | 5/2006 | Bleich |
| 2006/0095088 A1 | 5/2006 | DeRidder |
| 2006/0155344 A1 | 7/2006 | Rezai et al. |
| 2006/0161235 A1 | 7/2006 | King |
| 2006/0167525 A1 | 7/2006 | King |
| 2006/0195169 A1 | 8/2006 | Gross et al. |
| 2006/0200121 A1 | 9/2006 | Mowery |
| 2006/0206118 A1 | 9/2006 | Kim et al. |
| 2006/0241716 A1 | 10/2006 | Finch et al. |
| 2006/0247750 A1 | 11/2006 | Seifert et al. |
| 2007/0043400 A1 | 2/2007 | Donders et al. |
| 2007/0060954 A1 | 3/2007 | Cameron et al. |
| 2007/0123954 A1 | 5/2007 | Gielen et al. |
| 2007/0179579 A1 | 8/2007 | Feler et al. |
| 2007/0213671 A1 | 9/2007 | Hiatt |
| 2007/0255366 A1 | 11/2007 | Gerber et al. |
| 2007/0270928 A1 | 11/2007 | Erlebacher |
| 2007/0276319 A1 | 11/2007 | Betts |
| 2008/0009927 A1 | 1/2008 | Vilims |
| 2008/0033431 A1 | 2/2008 | Jung et al. |
| 2008/0039916 A1 | 2/2008 | Colliou et al. |
| 2008/0103572 A1 | 5/2008 | Gerber |
| 2008/0103579 A1 | 5/2008 | Gerber |
| 2008/0103580 A1 | 5/2008 | Gerber |
| 2008/0119711 A1 | 5/2008 | Nikumb et al. |
| 2008/0154349 A1 | 6/2008 | Rossing et al. |
| 2008/0188916 A1 | 8/2008 | Jones et al. |
| 2009/0204173 A1 | 8/2009 | Fang et al. |
| 2010/0179562 A1 | 7/2010 | Linker et al. |
| 2010/0249875 A1 | 9/2010 | Kishawi et al. |
| 2010/0292769 A1 | 11/2010 | Brounstein et al. |
| 2011/0184486 A1 | 7/2011 | De Ridder |
| 2012/0197370 A1 | 8/2012 | Kim et al. |
| 2012/0277839 A1 | 11/2012 | Kramer et al. |
| 2012/0283697 A1 | 11/2012 | Kim et al. |
| 2012/0310140 A1 | 12/2012 | Kramer et al. |
| 2013/0165991 A1 | 6/2013 | Kim et al. |
| 2013/0345783 A1 | 12/2013 | Burdulis |
| 2014/0343624 A1 | 11/2014 | Kramer |
| 2015/0151126 A1 | 6/2015 | Kishawi et al. |
| 2015/0165193 A1 | 6/2015 | Imran |

FOREIGN PATENT DOCUMENTS

| | | |
|---|---|---|
| CN | 101678204 A | 3/2010 |
| EP | 0779080 A | 6/1997 |
| EP | 1304135 A2 | 4/2003 |
| JP | 03041191 B2 | 6/1991 |
| JP | H06-218064 A | 8/1994 |
| JP | 8500996 A | 2/1996 |
| JP | 8080353 A | 3/1996 |
| JP | 10243954 A | 9/1998 |
| JP | 2004512105 | 4/2004 |
| JP | 2006523215 | 10/2004 |
| JP | 2005516697 | 6/2005 |
| JP | 2006508768 | 3/2006 |
| JP | 2008526299 | 7/2008 |
| JP | 2009539425 A | 11/2009 |
| JP | 2009539426 A | 11/2009 |
| WO | WO 02096512 A1 | 12/2002 |
| WO | WO 03/018113 A1 | 3/2003 |
| WO | WO 03/043690 A1 | 5/2003 |
| WO | WO 03/063692 | 8/2003 |
| WO | WO 03/066154 A2 | 8/2003 |
| WO | WO 03/084433 A2 | 10/2003 |
| WO | WO 03/090599 A2 | 11/2003 |
| WO | WO 2005/092432 A1 | 10/2005 |
| WO | WO 2006/033039 A1 | 3/2006 |
| WO | WO 2006/084635 A2 | 8/2006 |

OTHER PUBLICATIONS

Burton et al.; The organization of the seventh lumbar spinal ganglion of the cat; J Comp Neurol.; 149(2); pp. 215-232; May 15, 1973.

Ma et al.; Enhanced excitability of dissociated primary sensory neurons after chronic compression of the dorsal root ganglion in the rat; Pain; 113(1-2); pp. 106-112; Jan. 2005.

Myles et al.; Effects of different methods of peripheral nerve repair on the number and distribution of muscle afferent neurons in rat dorsal root ganglion; J Neurosurg; 77(3); pp. 457-462; Sep. 1992.

Prats-Galino et al.Prats; Representations of hindlimb digits in rat dorsal root ganglia; J Comp Neurol; 408(1); pp. 137-145; May 24, 1999.

Waxman et al.; Sodium channels, excitability of primary sensory neurons, and the molecular basis of pain; Muscle Nerve; 22(9); pp. 1177-1187; Sep. 1999.

Wessels et al.; A rostrocaudal somatotopic organization in the brachial dorsal root ganglia of neonatal rats; Clin Neurol Neurosurg; 95 Suppl; pp. S3-S11; 1993.

Wessels et al.; Evidence for a rostrocaudal organization in dorsal root ganglia during development as demonstrated by intra-uterine WGA-HRP injections into the hindlimb of rat fetuses; Brain Res Dev Brain Res; 54(2); pp. 273-281; Jul. 1, 1990.

Wessels et al.; Somatotopic organization in the sensory innervation of the rat hindlimb during development, using half dorsal root ganglia as subsegmental units; Eur J Morphol; 28(2-4); pp. 394-403; 1990.

Wessels et al.; The rostrocaudal organization in the dorsal root ganglia of the rat: a consequence of plexus formation?; Anat Embryol (Berl); 190(1); pp. 1-11; Jul. 1994.

Imran et al.; U.S. Appl. No. 12/607,009 entitled "Selective stimulation systems and signal parameters for medical conditions," filed Oct. 27, 2009.

Kim et al.; U.S. Appl. No. 12/369,706 entitled "Methods for stimulating a dorsal root ganglion," filed Feb. 11, 2009.

Nannini et al.; Muscle recruitment with intrafascicular electrodes; IEEE Trans on Biomedical Engineering; vol. 38; No. 8; pp. 769-776 Aug. 1991.

Imran et al; U.S. Appl. No. 11/952,062 entitled "Implantable flexible circuit leads and methods of use," filed Dec. 6, 2007.

Imran, Mir; U.S. Appl. No. 11/952,049, entitled "Grouped leads for spinal stimulation," filed Dec. 6, 2006.

Imran, Mir; U.S. Appl. No. 11/952,053 entitled "Delivery devices, systems and methods for stimulating nerve tissue on multiple spinal levels," filed Dec. 6, 2007.

Burdulis, Albert; U.S. Appl. No. 11/952,081 entitled "Hard tissue anchors and delivery devices," filed Dec. 6, 2007.

Imran et al; U.S. Appl. No. 12/022,135 entitled "Sutureless lead retention features," filed Jan. 29, 2008.

Advanced Neuromodulation Systems, Inc. (ANSI) Research Briefing dated Aug. 20, 2004 by Stephens Inc. Investment Bankers pp. 1-4.

(56) References Cited

OTHER PUBLICATIONS

Advanced Neuromodulation Systems, Inc. (ANSI) Research Bulletin dated Jul. 2, 2004 by Stephens Inc. Investment Bankers pp. 1-7.
Advanced Neuromodulation Systems, Inc. (ANSI) Research Bulletin dated Jul. 27, 2004 by Stephens Inc. Investment Bankers pp. 1-9.
Advanced Neuromodulation Systems, Inc. Equity Research dated Jan. 16, 2003 by Pacific Growth Equities pp. 1-8.
Alo, Kenneth M. 2002. New Trends in Neuromodulation for the Management of Neuropathic Pain. Neurosurgery. 50 (4): 690-703.
Aoki, Yasuchika et al. 2004. Distribution and Immunocytochemical Characterization of Dorsal Root Ganglion Neurons Innervating the Lumbar Intervertebral Disc in Rats: A Review. Life Sciences. 74 (21): 2627-2642.
Askar, Zahid, et al. 2003. Scott Wiring for Direct Repair of Lumbar Spondylolysis. Spine. 28 (4): 354-357.
Baba, Hiroshi et al. 1999. Peripheral Inflammation Facilitates Aβ Fiber-Mediated Synaptic Input to the Substantia Gelatinosa of the Adult Rat Spinal Cord. The Journal of Neuroscience. 19 (2): 859-867.
Bajwa, Zahid H. et al. 2001. Herpetic Neuralgia: Use of Combination Therapy for Pain Relief in Acute and Chronic Herpes Zoster. Geriatrics. 56 (12): 18-24.
Barendse, G.A. et al. 2001. Randomized Controlled Trial of Percutaneo Intradiscal Radiofrequency Thermocoagulation for Chronic Discogenic Back Pain: Lack of Effect From a 90-Second 70 C Lesion, Spine. 26 (3): 287-92. (Abstract Only).
Barlocher, C.B. et al. 2003. Kryorhizotomy: An Alternative Technique for Lumbar Medial Branch Rhizotomy in Lumbar Facet Syndrome. J Neurosurg. 98 (1): 14-20. (Abstract Only).
Blau, A. et al. 1997. Characterization and Optimization of Microelectrode Arrays for in Vivo Nerve Signal Recording and Stimulation. Biosens Bioelectron.12 (9-10): 883-92. (Abstract Only).
Boston Scientific a Neuromodulation Primer dated Jun. 9, 2004 in Medical Supplies and Devices, published by Susquehanna Financial Group, LLLP pp. 1-17.
Brammah, T.B. et al. 1994. Syringomyelia as a Complication of Spinal Arachnoiditis. Spine. 19 (22): 2603-5. (Abstract Only).
Braverman D.L. et al. 2001. Using Gabapentin to Treat Failed Back Surgery Syndrome Caused by Epidural Fibrosis: A Report of 2 Cases. Arch Phys Med Rehabil. 82 (5): 691-3. (Abstract Only).
Carlton, Susan M. et al. 2001. Tonic Control of Peripheral Cutaneo Nociceptors by Somatostatin Receptors. Journal of Neuroscience. 21 (11): 4042-4049.
Chaplan, S.R. et al. 1994. Quantitative Assessment of Tactile Allodynia in the Rat Paw. Journal of Neuroscience Methods. 53 (1): 55-63.
Cho, J. 1997. Percutaneo Radiofrequency Lumbar Facet Rhizotomy in Mechanical Low Back Pain Syndrome. Stereotact Funct Neurosurg. 68 (1-4): 212-7. (Abstract Only).
Crampon, M.-A. et al. 2002. Nerve Cuff Electrode With Shape Memory Alloy Armature: Design and Fabrication. Bio-Medical Materials and Engineering. 12 (4): 397-410.
Cuoco, Jr., Frank A. et al. 2000. Measurement of External Pressures Generated by Nerve Cuff Electrodes. IEEE Transactions on Rehabilitation Engineering. 8 (1): 35-41.
Cyberonics, Inc. Equity Research dated Jan. 16, 2003 by Pacific Growth Equities pp. 1-14.
Denny, N.M. et al. 2003. Evaluation of an Insulated Tuohy Needle System for the Placement of Interscalene Brachial Plex Catheters. Anaesthesia. 58 (6): 554-7. (Abstract Only).
Dreyfuss, Paul et al. 2000. Efficacy and Validity of Radiofrequency Neurotomy for Chronic Lumbar Zygopophysial Joint Pain. Spine. 25 (10): 1270-1277.
Dubuisson, D. 1995. Treatment of Occipital Neuralgia by Partial Posterior Rhizotomy at C1-3. J Neurosurg. 82 (4): 581-6. (Abstract Only).
Eschenfelder, Sebastian et al. 2000. Dorsal Root Section Elicits Signs of Neuropathic Pain Rather than Reversing Them in Rats With L5 Spinal Nerve Injury. Pain. 87 (2): 213-219.

Firth, Ava et al. 1999. Development of a Scale to Evaluate Postoperative Pain in Dogs. J Am Vet Med Assoc. 214 (5): 651-659.
Garcia Cosamalon, P. J. et al. 1991. Dorsal Percutaneo Radiofrequency Rhizotomy Guided With CT Scan in Intercostal Neuralgias. Technical note. Acta Neurochir (Wien). 109 (3-4): 140-1.
Giorgi, C. et al. 1984. Surgical Treatment of Glossopharyngeal Neuralgia and Pain From Cancer of the Nasopharynx. A 20-Year Experience. J Neurosurg. 61 (5): 952-5. (Abstract Only).
Gocer, A.I. et al. 1997. Percutaneo Radiofrequency Rhizotomy of Lumbar Spinal Facets the Results of 46 cases. Neurosurg Rev. 20 (2): 114-6. (Abstract Only).
Haller, H. et al. Treatment of Chronic Neuropathic Pain After Traumatic Central Cervical Cord Lesion with Gabapentin. Journal of Neural Transmission. 110 (9): 977-981.
Herron, L.D. 1989. Selective Nerve Root Block in Patient Selection for Lumbar Surgery: Surgical Results. J Spinal Disord. 2 (2): 75-9. (Abstract Only).
Higuchi, Yoshinori, et al. 2002. Exposure of the Dorsal Root Ganglion in Rats to Pulsed Radiofrequency Currents Activates Dorsal Horn Lamina I and II Neurons. Neurosurgery. 50 (4): 850-856.
Holsheimer, J. et al. 1995. Effects of Electrode Geometry and Combination on Nerve Fibre Selectivity in Spinal Cord Stimulation. Medical & Biological Engineering & Computing. 33 (5): 676-682.
Igarashi, T. et al. 2004. Lysis of Adhesions and Epidural Injection of Steroid/Local Anaesthetic During Epiduroscopy Potentially Alleviate Low Back and Leg Pain in Elderly Patients With Lumbar Spinal Stenosis. British Journal of Anaesthesia. 93 (2): 181.
Julius, David et al. 2001. Molecular Mechanisms of Nociception. Nature. 413 (6852): 203-210.
Kanpolat, Yucel et al. 2001. Percutaneo Controlled Radiofrequency Trigeminal Rhizotomy for the Treatment of Idiopathic Trigeminal Neuralgia: 25-Year Experience with 1600 Patients. Neurosurgery. 48 (3): 524-534.
Kapadia, N.P. et al. 2000. Gabapentin for Chronic Pain in Spinal Cord Injury: A Case Report. Arch Phys Med Rehabil. 81 (10): 1439-41. (Abstract Only).
Kapoor, Vibhu et al. 2003. Refractory Occipital Neuralgia: Preoperative Assessment With CT-Guided Nerve Block Prior to Dorsal Cervical Rhizotomy. American Journal of Neuroradiology. 24 (10): 2105-10.
Karai, Laszlo et al. 2004. Deletion of Vanilloid Receptor 1-Expressing Primary Afferent Neurons for Pain Control. Journal of Clinical Investigation. 113 (9): 1344-1352.
Kline, David G. et al. 1998. Management and Results of Sciatic Nerve Injuries: a 24-Year Experience. Journal of Neurosurgery. 89 (1): 13-23.
Kobayashi, Shigeru et al. 2004. Pathology of Lumbar Nerve Root Compression Part 1: Intraradicular Inflammatory Changes Induced by Mechanical Compression. Journal of Orthopaedic Research. 22 (1): 170-179.
Kobayashi, Shigeru et al. 2004. Pathology of Lumbar Nerve Root Compression Part 2: Morphological and Immunohistochemical Changes of Dorsal Ganglion. Journal of Orthopaedic Research. 22 (1): 180-188.
Koszewski, W. et al. 2003. [The DREZ Lesion as an Effective Treatment for Chronic Hypothetically Post-Herpetic Neuropathic Pain. Case Report and Review of Literature]. Neurol Neurochir Pol. 37 (4): 943-53. (Abstract Only).
Lawrence, Stephen M. et al. 2002. Long-Term Biocompatibility of Implanted Polymer-Based Intrafascicular Electrodes. Journal of Biomedical Materials Research. 63 (5): 501-506.
Lee, In-Seop et al. 2002. Characterization of Iridium Film as a Stimulating Neural Electrode. Biomaterials. 23 (11):2375-2380.
Lew, Henry L. et al. 2004. Preganglionic Approach to Transforaminal Epidural Steroid Injections. Am. J. Phys. Med. Rehabil. 83 (5): 378.
Maher, C.O. et al. 1999. Lateral Exit-Zone Stenosis and Lumbar Radiculopathy. J Neurosurg. 90 (1): 52-8. (Abstract Only).
Mailley, Sophie et al. 2004. Thin Film Platinum Cuff Electrodes for Neurostimulation: In Vitro Approach of Safe Neurostimulation Parameters. Bioelectrochemistry. 63: 359-364.

(56) References Cited

OTHER PUBLICATIONS

Masini, Michelle et al. 1996. Activated Pyrolytic Carbon Tip Pacing Leads: An Alternative to Steroid-Eluting Pacing Leads? PACE. 1: 1832-1835.
Medtronic, Inc. Equity Research dated Dec. 18, 2002 by Pacific Growth Equities pp. 1-20.
Medtronic. Analysis of Sales/Earnings-F1Q05: Many Gives and Takes in the Quarter dated Aug. 20, 2004 by Morgan Stanley pp. 1-25.
Methods of Placement of Neurostimulation Lead, Infusion, Catheter, and/or Sensor Via Peripheral Vasculature. From IP.com PriorArtDatabase—Apr. 10, 2003—#000012136 http://www.priorartdatabase.com/IPCOM/000012136.
Modem Ideas: The Gate Control Theory of Chronic Pain. Spine-Health.com: Your Comprehensive Resource for Back Pain. http://www.spine-health.com/topics/cd/pain/chronic_pain_theories/chronic_pain_theory02.html (accessed Feb. 24, 2006).
Mond, Harry G. et al. 2004. Implantable Transveno Pacing Leads: The Shape of Things to Come. PACE. 27: 887-893.
Monti, Enrico. 2004. Peripheral Nerve Stimulation: A Percutaneo Minimally Invasive Approach. Neuromodulation. 7 (3): 193. (Abstract Only).
Naples, Gregory G. 1988. A Spiral Nerve Cuff Electrode for Peripheral Nerve Stimulation. IEEE Transactions on Biomedical Engineering. 35 (11): 905-916.
Narozny, Martin et al. 2001. Therapeutic Efficacy of Selective Nerve Root Blocks in the Treatment of Lumbar Radicular Leg Pain. Swiss Med Wkly. 131 (5-6): 75-80.
Nashold, Blaine S. et al. 1979. Peripheral Nerve Stimulation for Pain Relief Using a Multicontact Electrode System. Technical note. Journal of Neurosurgery. 51 (6): 872-873.
Nashold, Blaine S. et al. 1982. Long-Term Pain Control by Direct Peripheral-Nerve Stimulation. The Journal of Bone and Joint Surgery. 64 (1): 1-10.
Neumann, Simona et al. 2002. Regeneration of Sensory Axons Within the Injured Spinal Cord Induced by Intraganglionic cAMP Elevation. Neuron. 34 (6): 885-93.
Nielson, K.D. et al. 1976. Peripheral Nerve Injury From Implantation of Chronic Stimulating Electrodes for Pain Control. Surg Neurol. 5 (1): 51-3. (Abstract Only).
North, Richard B. et al. 1991. Dorsal Root Ganglionectomy for Failed Back Surgery Syndrome: A 5-Year Follow-Up Study. J Neurosurg. 74: 236-242.
North, Richard B. et al. 2000. Chapter 123: Current Concepts in the Neurosurgical Management of Persistent Pain (pp. 1634-1637). Operative Neurosurgical Techniques 4th Edition (Henry H. Schmidek et al. eds.). Philadelphia: W.B. Saunders Company.
Nygaard, Oystein P. et al. 1998. The Function of Sensory Nerve Fibers in Lumbar Radiculopathy: Use of Quantitative Sensory Testing in the Exploration of Different Populations of Nerve Fibers and Dermatomes. Spine. 23 (3): 348-352.
Obata, K. et al. 2004. Activation of Extracellular Signal-Regulated Protein Kinase in the Dorsal Root Ganglion Following Inflammation Near the Nerve Cell Body. Neuroscience. 126 (4): 1011-1021.
Obata, Koichi et al. 2002. Expression of Neurotrophic Factors in the Dorsal Root Ganglion in a Rat Model of Lumbar Disc Herniation. Pain. 99 (1-2): 121-132.
Olby, Natasha J. et al, 2001. Development of a Functional Scoring System in Dogs With Acute Spinal Cord Injuries. Am J Vet Res. 62 (10): 1624-1628.
Parlier-Cuau, Caroline et al. 1999. Symptomatic Lumbar Facet Joint Synovial Cysts: Clinical Assessment of Facet Joint Steroid Injection After 1 and 6 Months and Long-Term Follow-Up in 30 Patients. Radiology. 210 (2): 509-513.
Pedrolli, C. et al. 1990. [Dorsolumbar Arachnoid Cysts. A Case Report]. Recenti Prog Med. 81 (11): 699-701. (Abstract Only).
Rodriguez, Francisco J. et al. 2000. Polyimide Cuff Electrodes for Peripheral Nerve Stimulation. Journal of Neuroscience Methods. 98 (2): 105-118.
Rokugo, Tomoyuki et al. 2002. A Histochemical Study of Substance P in the Rat Spinal Cord: Effect of Transcutaneo Electrical Nerve Stimulation. J Nippon Med Sch. 69 (5): 428-433.
Romero, E. et al. 2001. Neural Morphological Effects of Long-Term Implantation of the Self-Sizing Spiral Cuff Nerve Electrode. Medical & Biological Engineering & Computing. 39 (1): 90-100.
Rongstad, K. et al. 1996. Popliteal Sciatic Nerve Block for Postoperative Analgesia. Foot Ankle Int. 17 (7): 378-82. (Abstract Only).
Ruetten, S. et al. 2003. Endoscopic Surgery of the Lumbar Epidural Space (Epiduroscopy): Results of Therapeutic Intervention in 93 Patients. Minim Invasive Neurosurg. 46 (1): 1-4. (Abstract Only).
Sairyo, K. et al. 2003. A New Endoscopic Technique to Decompress Lumbar Nerve Roots Affected by Spondylolysis. Technical Note. J Neurosurg. 98 (3): 290-3. (Abstract Only).
Salame, K. et al. 2003. Surgical Treatment of Spasticity by Selective Posterior Rhizotomy 30 Years Experience. Isr Med Assoc J. 5 (8): 543-6. (Abstract Only).
Saris, S.C. et al. 1986. Sacrococcygeal Rhizotomy for Perinea Pain. Neurosurgery. 19 (5): 789-93. (Abstract Only).
Sauvage, P.J. et al. 2000. Intraspinal Synovial Cysts of the Lumbar Spine: Imaging Findings and Treatment by Percutaneo Steroid Injection. Review of 13 Cases. [Kystes Synoviaux Intraspinaux Lombaires: Imagerie et Traitement Par Infiltration. A Propos De.
Schwartzman, Robert J. et al. 2001. Neuropathic Central Pain: Epidemiology, Etiology, and Treatment Options. Arch Neurol. 58 (10): 1547-1550.
Sedan, R. et al. 1978. Therapeutic Electrical Neurostimulation. French Language Society of Neurosurgery—28th Annual Congress—Athens, May 29-30, 1978. Neurochirurgie. 24: 3-& Suppl. 1 (in French with English Summary pp. 121-125.
Sheth, Rishi N. et al. 2002. Mechanical Hyperalgesia After an L5 Ventral Rhizotomy or an L5 Ganglionectomy in the Rat. Pain. 96: 63-72.
Siddall, Philip J. et al. 2004. Persistent Pain as a Disease Entity: Implications for Clinical Management. Anesth Analg. 99: 510-20.
Silvers, H.R. 1990. Lumbar Percutaneo Facet Rhizotomy. Spine.15 (1): 36-40. (Abstract Only).
Slappendel, R. et al. 1997. The efficacy of Radiofrequency Lesioning of the Cervical Spinal Dorsal Root Ganglion in a Double Blinded Randomized Study: No difference Between 40 Degrees C and 67 Degrees C Treatments. Pain. 73 (2): 159-63. (Abstract Only).
Sluijter, Menno E. et al. 1998. The Effects of Pulsed Radiofrequency Fields Applied to the Dorsal Root Ganglion—A Preliminary Report. The Pain Clinic.11 (2): 109-117.
Smith, H.P. et al. 1981. Radiofrequency Neurolysis in a Clinical Model: Neuropathological Correlation. J Neurosurg. 55 (2): 246-53. (Abstract Only).
Spaic, M. et al. 1999. Drez Surgery on Con Medullaris (After Failed Implantation of Vascular Omental Graft) for Treating Chronic Pain Due to Spine (Gunshot) Injuries. Acta Neurochir(Wein). 141(12): 1309-1312.
Spaic, M. et al. 2002. Microsurgical DREZotomy for Pain of Spinal Cord and Cauda Equina Injury Origin: Clinical Characteristics of Pain and Implications for Surgery in a Series of 26 Patients. Acta Neurochir (Wien). 144 (5): 453-462.
Stanton-Hicks, M. et al. 1997. Stimulation of the Central and Peripheral Nervo System for the Control of Pain. Journal of Clinical Neurophysiology. 14 (1): 46-62.
Steinbok, P. et al. 1998. Complications After Selective Posterior Rhizotomy for Spasticity in Children With Cerebral Palsy. Pediatr Neurosurg. 28 (6): 300-13. (Abstract Only).
Stolker, Robert J. et al. 1994. The Treatment of Chronic Thoracic Segmental Pain by Radiofrequency Percutaneo Partial Rhizotomy. J Neurosurg. 80 : 986-992.
Strait, T.A. et al. 1981. Intraspinal Extradural Sensory Rhizotomy in Patients With Failure of Lumbar Disc Surgery. J Neurosurg. 54 (2): 193-6. (Abstract Only).
Taha, J.M. et al. 1995. Long-Term Results of Radiofrequency Rhizotomy in the Treatment of Cluster Headache. Headache. 35 (4): 193-6. (Abstract Only).

(56) References Cited

OTHER PUBLICATIONS

Taub, Arthur et al. 1995. Dorsal Root Ganglionectomy for Intractable Monoradicular Sciatica: A Series of 61 Patients. Stereotact Funct Neurosurg. 65 (1-4): 106-110.
Uematsu, Sumio. 1988. Chapter 106: Percutaneo Electrothermocoagulation of Spinal Nerve Trunk, Ganglion, and Rootlets (pp. 1207-1221). Operative Neurosurgical Techniques, Indications, Methods and Results 2nd edition. (Henry H. Schmidek et al. eds.). P.
Van Zundert, Jan et al. 2005. Pulsed Radiofrequency in Chronic Pain Management: Looking for the Best Use of Electrical Current. World Institute of Pain. 5 (2): 74-76.
Van De Kraats, Everine B. et al. 2004. Noninvasive Magnetic Resonance to Three-Dimensional Rotational X-Ray Registration of Vertebral Bodies for Image-Guided Spine Surgery. Spine. 29 (3): 293-297.
Van Kleef, M. et al. 1993. Effects and Side Effects of a Percutaneo Thermal Lesion of the Dorsal Root Ganglion in Patients with Cervical Pain Syndrome. Pain. 52 (1): 49-53.
Van Kleef, M. et al. 1996. Radiofrequency Lesion Adjacent to the Dorsal Root Ganglion for Cervicobrachial Pain: A Prospective Double Blind Randomized Study. Neurosurgery. 38 (6): 1127-31.
Van Kleef, Maarten et al. 1998. Chapter 160: Radiofrequency Lesions in the Treatment of Pain of Spinal Origin (pp. 1585-1599). Textbook of Stereotactic and Functional Neurosurgery 1st Edition. (Philip L. Gildenberg et al. eds.). New York: McGraw-Hill.
Van Zundert, J. et al. 2005. Pulsed and Continuo Radiofrequency Current Adjacent to the Cervical Dorsal Root Ganglion of the Rat Induces Late Cellular Activity in the Dorsal Horn. Anesthesiology. 102 (1): 125-31.
Vaughan, R. 1975. Percutaneo Radiofrequency Gangliotomy in the Treatment of Trigeminal Neuralgia and Other Facial Pain. Aust N Z J Surg. 45 (2): 203-7. (Abstract Only).
Viton, J.-M. et al. 1998. Short-Term Assessment of Periradicular Corticosteroid Injections in Lumbar Radiculopathy Associated With Disc Pathology. Neuroradiology. 40 (1): 59-62.
Viton, J.M. et al. 1998. Short-Term Evaluation of Periradicular Corticosteroid Injections in the Treatment of Lumbar Radiculopathy Associated With Disc Disease. Rev Rhum Engl Ed. 65 (3): 195-200. (Abstract Only).
Wagner, A.L. et al. 2002. Selective Nerve Root Blocks. Tech Vasc Interv Radiol. 5 (4): 194-200. (Abstract Only).
Weiner, Richard L. 2000. The Future of Peripheral Nerve Neurostimulation. Neurological Research. 22 (3): 299-304.
Weiner, Richard L. 2003. Peripheral Nerve Neurostimulation. Neurosurgery Clinics of North America. 14 (3): 401-408.
Weinstein, James et al. 1988. The Pain of Discography. Spine. 13(12):1344-8.
Wetzel, F. Todd et al. 1997. Extradural Sensory Rhizotomy in the Management of Chronic Lumbar Radiculopathy: A Minimum 2-Year Follow-up Study. Spine. 22 (19): 2283-2291.
Wetzel, F.T. 1992. Chronic Benign Cervical Pain Syndromes: Surgical Considerations. Spine. 17 (10): S367-74, (Abstract Only).
Wetzel, F.T. et al. 1992. The Treatment of Chronic Extremity Pain in Failed Lumbar Surgery. The Role of Lumbar Sympathectomy. Spine. 17 (12): 2367-8. (Abstract Only).
White, P.F. et al. 2003. The Use of a Continuo Popliteal Sciatic Nerve Block After Surgery Involving the Foot and Ankle: Does It Improve the Quality of Recovery? Anesth Analg. 97 (5): 1303-9. (Abstract Only).
Whitworth, Louis Anthony et al. 2002. Application of Spinal Ablative Techniques for the Treatment of Benign Chronic Painful Conditions. Spine. 27 (22): 2607-2612.
Wilkinson, H.A. et al. 2001. Sensory Ganglionectomy: Theory, Technical Aspects, and Clinical Experience. J Neurosurg. 95 (1): 61-6. (Abstract Only).
Wong, C.B. et al. 2002. Clinical Outcomes of Revision Lumbar Spinal Surgery: 124 Patient With a Minimum of Two Years of Follow-Up. Chang Gung Med J. 25 (3): 175-82. (Abstract Only).
Wright, Robert E. et al. 1998. Neurostimulation of the L2 Dorsal Root Ganglion for Intractable Disc Pain: Description of a Novel Technique. Presented at the IFESS.
Wu, Gang et al. 2001. Early Onset of Spontaneo Activity in Uninjured C-Fiber Nociceptors After Injury to Neighboring Nerve Fibers. Journal of Neuroscience. 21 (8): RC140.
Yamashita, Toshihiko et al. 2002. A Quantitative Analysis of Sensory Function in Lumbar Radiculopathy Using Current Perception Threshold Testing. Spine. 27 (14): 1567-1570.
Yoshida, Hirotoshi et al. 1997. Lumbar Nerve Root Compression Caused by Lumbar Intraspinal Gas: Report of Three Cases. Spine.22 (3): 348-351.
Young, R.F. 1996. Chapter 161: Dorsal Rhizotomy and Dorsal Root Ganglionectomy (pp. 3442-3451). Neurological Surgery 4th Edition. (Julian R. Youmans ed.). Philadelphia: W.B. Saunders Company.
Kim et al; U.S. Appl. No. 12/051,770 entitled "Neurostimulation system," filed Mar. 19, 2008.
Burdulis, Albert G.; U.S. Appl. No. 13/175,488 entitled "Hard Tissue anchors and delivery devices," filed Jul. 1, 2011.
Grigsby et al.; U.S. Appl. No. 13/104,787 entitled "Methods, systems and devices for reducing migration," filed May 10, 2011.
Kocsis et al.; NR2B receptors are involved in the mediation of spinal segmental reflex potentials but not in the cumulative motoneuronal depolarization in vitro; Brain Research Bulletin, Elsevier Science Ltd.; vol. 64; No. 2; pp. 133-138; Aug. 30, 2004.
Lopez et al.; Excitatory and inhibitory effects of serotonin on spinal nociceptive reflexes are mediated by 5-HT2 and 5-HT1B receptors; (Database Biosis Biosciences information service, Philadelphia, PA, US, XP002567533, accession No. PREV200100573757); Abstract; 2001.
Kramer et al.: U.S. Appl. No. 13/365,163 entitled "Devices, Systems and Methods for the Targeted Treatment of Movement Disorders," filed Feb. 2, 2012.
Horsch, S. et al. Epidural spinal cord stimulation in the treatment of severe peripheral arterial occlusive disease; Annals of Vascular Surgery; 8(5): 468-74. Sep. 1994.
Mayfield Clinic for Brain & Spine; printed from http://www.mayfieldclinic.com/PE-AnatSpine.htm (last updated Jan. 2013); 7 pages.
Medicinenet.com; Definition of Lateral; printed from http://www.medterms.com/script/main/art.asp?articlekey=6226 (on Jun. 4, 2014); 3 pages.
Kishawi et al.; U.S. Appl. No. 13/753,326 entitled "Pain management with stimulation subthreshold to parasthesia," filed Jan. 29, 2013.
Kim et al.; U.S. Appl. No. 14/216,805 entitled "Neurostimulation System," filed Mar. 17, 2014.
Wedley et al. Handbook of Clinical Techniques in the Management of Chronic Pain. Taylor & Francis; pp. 17-19. Nov. 27, 1996.
Dorsal Root Ganglion; www.biology-online.org/dDorsal_root_ganglion; downloaded Nov. 5, 2013; 4 pgs.
The Peripheral Nervous System; http://cnx.org/content/m44751/latest; downloaded Nov. 5, 2013; 7 pgs.
Clark, Robert K. "Anatomy and physiology: understanding the human body"; Jones & Bartlett Publishers; Sudbury, MA; ISBN 0-7637-4816-6; Chapter 12; pp. 213-215; Feb. 28, 2005.
Burdulis; U.S. Appl. No. 14/633,060 entitled "Hard tissue anchors and delivery devices," filed Feb. 26, 2015.
Imran et al.; U.S. Appl. No. 14/719,076 entitled "Sutureless lead retention features," filed May 21, 2015.
Kishawi et al.; U.S. Appl. No. 14/726,359 entitled "Selective stimulation systems and signal parameters for medical conditions," filed May 29, 2015.
Imran; U.S. Appl. No. 14/814,343 entitled "Grouped leads for spinal stimulation," filed Jul. 30, 2015.

* cited by examiner

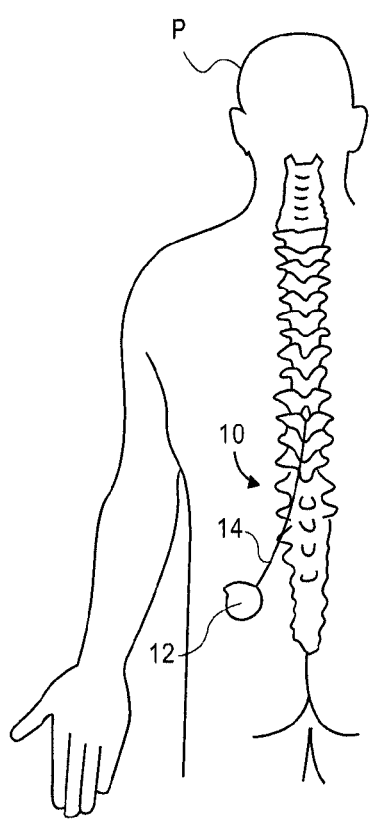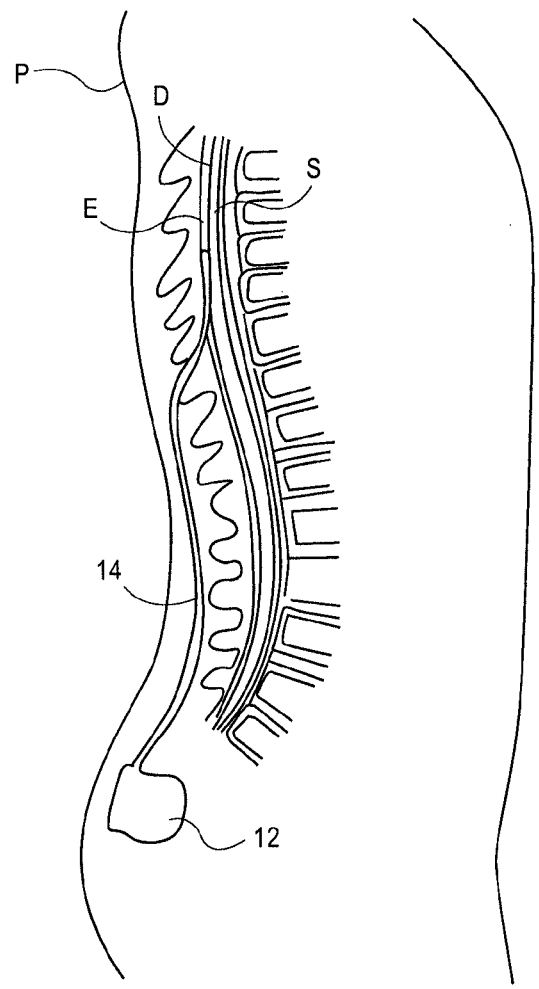
FIG. 1A
(PRIOR ART)
FIG. 1B
(PRIOR ART)

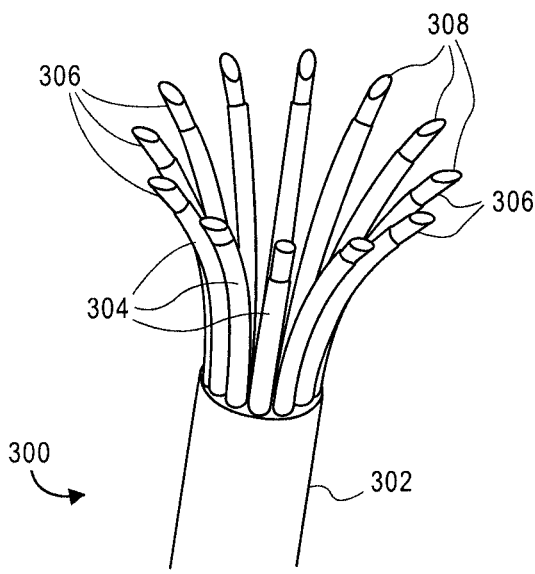
FIG. 8A
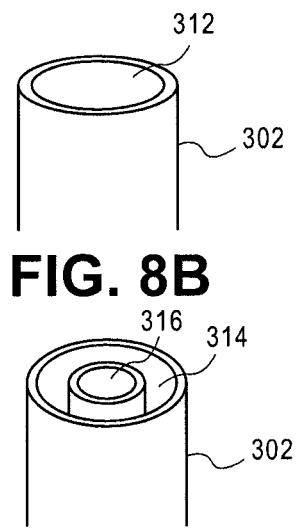
FIG. 8B
FIG. 8C
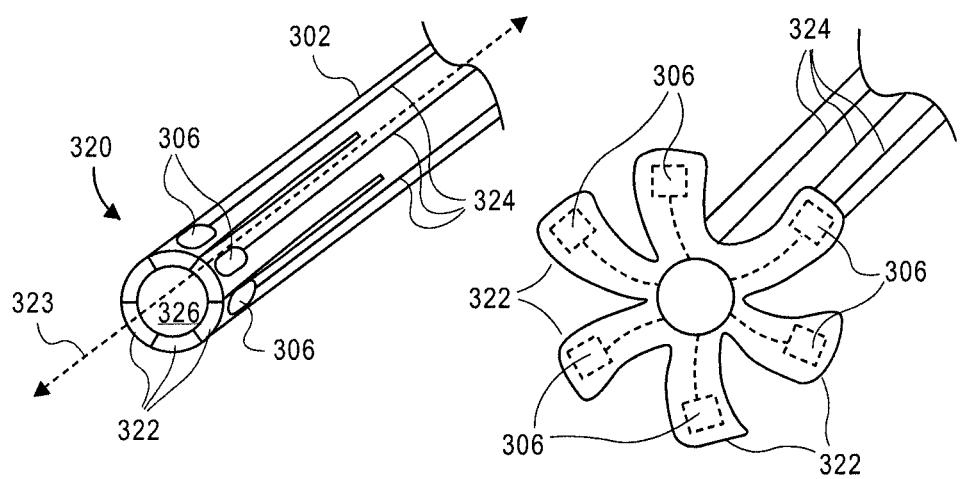
FIG. 9A
FIG. 9B

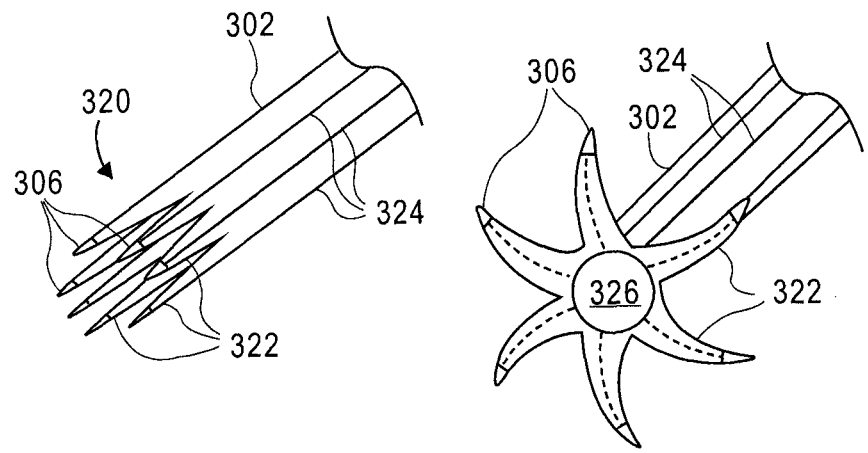
FIG. 10A
FIG. 10B
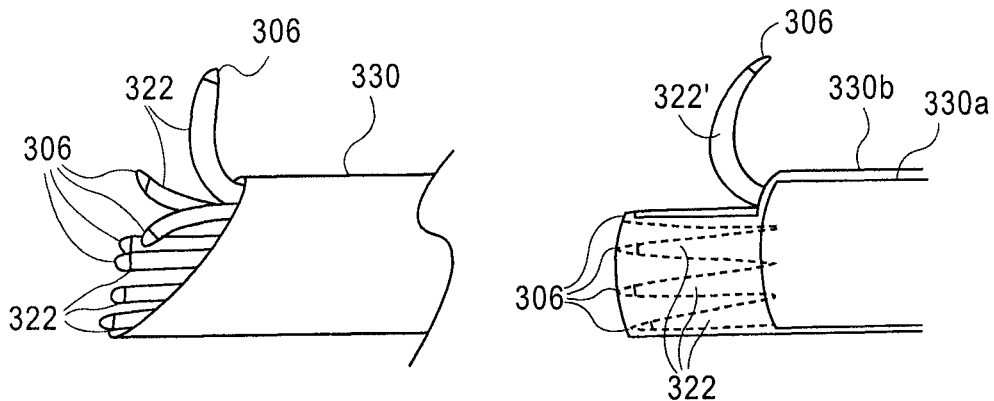
FIG. 10C
FIG. 10D

US 9,427,570 B2

EXPANDABLE STIMULATION LEADS AND METHODS OF USE

CROSS-REFERENCES TO RELATED APPLICATIONS

This application claims priority of provisional patent application No. 60/873,465, filed on Dec. 6, 2006, incorporated herein by reference for all purposes.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The application of specific electrical energy to the spinal cord for the purpose of managing pain has been actively practiced since the 1960s. It is known that application of an electrical field to spinal nervous tissue can effectively mask certain types of pain transmitted from regions of the body associated with the stimulated nervous tissue. Such masking is known as paresthesia, a subjective sensation of numbness or tingling in the afflicted bodily regions. Application of electrical energy has been based on the gate control theory of pain. Published in 1965 by Melzack and Wall, this theory states that reception of large nerve fiber information, such as touch, sense of cold, or vibration, would turn off or close the gate to reception of painful small nerve fiber information. The expected end result would, therefore, be pain relief. Based on the gate control theory, electrical stimulation of large fibers of the spinal cord cause small fiber information to be reduced or eliminated at that spinal segment and all other information downstream from that segment would be reduced or eliminated as well. Such electrical stimulation of the spinal cord, once known as dorsal column stimulation, is now referred to as spinal cord stimulation or SCS.

FIGS. 1A-1B illustrate conventional placement of an SCS system 10. Conventional SCS systems include an implantable power source or implantable pulse generator (IPG) 12 and an implantable lead 14. Such IPGs 12 are similar in size and weight to pacemakers and are typically implanted in the buttocks of a patient P. Using fluoroscopy, the lead 14 is implanted into the epidural space E of the spinal column and positioned against the dura layer D of the spinal cord S, as illustrated in FIG. 1B. The lead 14 is implanted either through the skin via an epidural needle (for percutaneous leads) or directly and surgically through a mini laminotomy operation (for paddle leads).

FIG. 2 illustrates example conventional paddle leads 16 and percutaneous leads 18. Paddle leads 16 typically have the form of a slab of silicon rubber having one or more electrodes 20 on its surface. Example dimensions of a paddle lead 16 is illustrated in FIG. 3. Percutaneous leads 18 typically have the form of a tube or rod having one or more electrodes 20 extending therearound. Example dimensions of a percutaneous lead 18 is illustrated in FIG. 4.

Implantation of a percutaneous lead 18 typically involves an incision over the low back area (for control of back and leg pain) or over the upper back and neck area (for pain in the arms). An epidural needle is placed through the incision into the epidural space and the lead is advanced and steered over the spinal cord until it reaches the area of the spinal cord that, when electrically stimulated, produces a comfortable tingling sensation (paresthesia) that covers the patient's painful area. To locate this area, the lead is moved and turned on and off while the patient provides feedback about stimulation coverage. Because the patient participates in this operation and directs the operator to the correct area of the spinal cord, the procedure is performed with local anesthesia.

Implantation of paddle leads 16 typically involves performing a mini laminotomy to implant the lead. An incision is made either slightly below or above the spinal cord segment to be stimulated. The epidural space is entered directly through the hole in the bone and a paddle lead 16 is placed over the area to stimulate the spinal cord. The target area for stimulation usually has been located before this procedure during a spinal cord stimulation trial with percutaneous leads 18.

Although such SCS systems have effectively relieved pain in some patients, these systems have a number of drawbacks. To begin, as illustrated in FIG. 5, the lead 14 is positioned upon the spinal cord dura layer D so that the electrodes 20 stimulate a wide portion of the spinal cord and associated spinal nervous tissue. The spinal cord is a continuous body and three spinal levels of the spinal cord are illustrated. For purposes of illustration, spinal levels are sub-sections of the spinal cord S depicting that portion where the dorsal root DR and ventral root VR join the spinal cord S. The peripheral nerve N divides into the dorsal root DR and the dorsal root ganglion DRG and the ventral nerve root VR each of which feed into the spinal cord S. An ascending pathway 17 is illustrated between level 2 and level 1 and a descending pathway 19 is illustrated from level 2 to level 3. Spinal levels can correspond to the veterbral levels of the spine commonly used to describe the vertebral bodies of the spine. For simplicity, each level illustrates the nerves of only one side and a normal anatomical configuration would have similar nerves illustrated in the side of the spinal cord directly adjacent the lead.

Motor spinal nervous tissue, or nervous tissue from ventral nerve roots, transmits muscle/motor control signals. Sensory spinal nervous tissue, or nervous tissue from dorsal nerve roots, transmit pain signals. Corresponding dorsal and ventral nerve roots depart the spinal cord "separately"; however, immediately thereafter, the nervous tissue of the dorsal and ventral nerve roots are mixed, or intertwined. Accordingly, electrical stimulation by the lead 14 often causes undesirable stimulation of the motor nerves in addition to the sensory spinal nervous tissue.

Because the electrodes span several levels the generated stimulation energy 15 stimulates or is applied to more than one type of nerve tissue on more than one level. Moreover, these and other conventional, non-specific stimulation systems also apply stimulation energy to the spinal cord and to other neural tissue beyond the intended stimulation targets. As used herein, non-specific stimulation refers to the fact that the stimulation energy is provided to all spinal levels including the nerves and the spinal cord generally and indiscriminately. Even if the epidural electrode is reduced in size to simply stimulate only one level, that electrode will apply stimulation energy indiscriminately to everything (i.e. all nerve fibers and other tissues) within the range of the applied energy. Moreover, larger epidural electrode arrays may alter cerebral spinal fluid flow thus further altering local neural excitability states.

Another challenge confronting conventional neurostimulation systems is that since epidural electrodes must apply energy across a wide variety of tissues and fluids (i.e. CSF fluid amount varies along the spine as does pia mater thickness) the amount of stimulation energy needed to provide the desired amount of neurostimulation is difficult to precisely control. As such, increasing amounts of energy may be required to ensure sufficient stimulation energy reaches the desired stimulation area. However, as applied stimulation energy increases so too increases the likelihood of deleterious damage or stimulation of surrounding tissue, structures or neural pathways.

Improved stimulation systems and methods are desired that enable more precise and effective delivery of stimulation energy. In particular, systems and methods which deliver stimulation energy to specific target tissue while minimizing delivery to tissue nearby. Such systems should be easily deliverable and accommodate various anatomies. At least some of these objectives will be met by the present invention.

BRIEF SUMMARY OF THE INVENTION

The present invention provides devices, systems and methods for stimulating a target tissue, particularly a target tissue which is small, not easily locatable or benefits from precise stimulation while minimizing stimulation of nearby tissues. An example of such a target tissue is a dorsal root, particularly a dorsal root ganglion (DRG), of a spinal anatomy. The dorsal root (or posterior root) is the afferent sensory root of a spinal nerve. Along the dorsal root is the DRG, which contains the neuron cell bodies of the nerve fibers conveyed by the root. Stimulation of the DRG itself blocks sensory pain signals providing relief to the patient. It is desired to focus stimulation onto the DRG while minimizing stimulation of surrounding tissue, particularly nearby spinal anatomy such as the ventral root which carries motor neurons. By focusing such stimulation, pain may be treated with minimal or no adverse affect on motor sensations. In order to most effectively stimulate the DRG while minimizing or excluding undesired stimulation of other anatomies, it may be desired to position a stimulation electrode as close as possible to the DRG (such as within 1 mm). This may be challenging when the exact location of the DRG is unknown or difficult to reach.

Specific DRGs may be challenging to locate in certain patients or under certain conditions. The DRG is surrounded by the bony anatomy of the vertebrae and is accessible via the spinal column or laterally through a foramen. Each approach involves careful navigation through the anatomy. The anatomies of both the vertebrae and the spinal tissue may vary from patient to patient and from spinal level to spinal level based on both natural variation and previous injury or disease progression. Such variation may impede easy and direct access to the DRG. Further, the DRG is a relatively small target which may be difficult to locate amidst its surrounding tissue. Thus, in some instances the exact location of the DRG may be unknown.

The devices, systems and methods of the present invention assist in stimulating such target tissues while minimizing stimulation of undesired non-target tissues. It may be appreciated that although the following examples are described and illustrated in relation to the DRG, the present invention may be used to stimulate any target tissue within the spinal anatomy, such as the dorsal root or the ventral root, or elsewhere in the general anatomy.

In a first aspect of the present invention, lead devices and systems are provided having one or more electrodes, wherein the electrodes are positionable in disperse locations within a specific target area. In some embodiments, at least some of the electrodes are independently positionable. And, in some embodiments, the position of at least some of the electrodes is adjustable. Some or all of the electrodes may be used to stimulate the desired tissue, such as to stimulate a specific portion of the target area. Or, the one or more electrodes that fall near the target tissue may be used to stimulate the tissue while the other electrodes are not used.

In a second aspect of the present invention, methods are provided for stimulating a target tissue. In some embodiments, such methods include advancing a shaft toward the target tissue, extending at least two electrode shafts from the shaft, wherein each electrode shaft has an electrode, positioning each electrode in proximity to the target tissue, and energizing at least one of the electrodes to stimulate the target tissue.

In preferred embodiments, the target tissue comprises a dorsal root ganglion. In some embodiments, energizing includes energizing a minimum number of electrodes to stimulate the dorsal root ganglion and not energizing remaining electrodes. Likewise, in some embodiments, energizing includes energizing at least one electrode positioned near the dorsal root ganglion and not energizing at least one other electrode positioned further way from the dorsal root ganglion.

Extending at least two electrode shafts from the shaft may include extending at least one of the electrode shafts radially outwardly from the shaft. In some instances, extending includes extending the at least two electrode shafts in directions at least 45 degrees apart. Or, extending may include extending the at least two electrode shafts in directions at least 90 degrees apart. Optionally, extending includes extending a plurality of electrode shafts in a circular configuration radially outwardly from the shaft.

The at least two electrode shafts may be extended through separate lumens in the shaft. Or, at least some of the at least two electrode shafts may be extended through a common lumen in the shaft. In some embodiments, positioning includes steering each electrode shaft. Optionally, positioning includes independently positioning each electrode shaft.

When approaching the target tissue, particularly a dorsal root ganglion, advancing may includes advancing the shaft through an epidural space. Or, advancing may include approaching the dorsal root ganglion from outside of a spinal column. In such instances, advancing may include advancing the shaft at least partially through a foramen.

In another aspect of the present invention, a lead is provided comprising a shaft having a distal end split into at least two finger portions, wherein the finger portions are movable radially outwardly from the shaft, and an electrode disposed on each finger portion. Typically, the at least two finger portions are alignable with a longitudinal axis of the shaft. In some embodiments, at least one finger portion is able to move radially outwardly, such as by recoil due to precurvature. In such embodiments, the lead may further comprise a sheath positionable at least partially over the distal end of the shaft so as to hold the at least two finger portions in alignment with the longitudinal axis and retractable to release the at least one precurved finger portion allowing recoil. Alternatively, the at least one finger portion includes a pull-wire to move radially outwardly. Optionally, the at least one finger portion is independently movable. The at least one finger portion may have a variety of shapes, including a pointed shape. Typically, the shaft includes a central lumen for the passage of tools and other devices.

In some embodiments, the shaft is configured for positioning at least one of the electrodes in proximity to a dorsal root ganglion. Optionally, the shaft may be configured for advancement through an epidural space. Additionally or alternatively, the shaft may be configured for advancement at least partially through a foramen.

In yet another aspect of the present invention, a system is provided comprising a shaft having a distal end split into at least two finger portions, wherein each finger portion has an electrode and each finger portions is movable radially outwardly from the shaft, and a first sheath positionable over the shaft so as to hold each finger portion in alignment with a longitudinal axis. In some embodiments, the first sheath is positionable so as to allow at least one finger portion to move radially outwardly from the shaft while maintaining another finger portion in longitudinal alignment. For example, the fi St sheath may have an angled distal end. Additionally or alternatively, the first sheath may have a cutout which allows the at least one finger portion to move radially outwardly from the shaft therethrough. Optionally, the system may include a second sheath positionable over the first sheath so as to retrain at least one finger portion.

Other objects and advantages of the present invention will become apparent from the detailed description to follow, together with the accompanying drawings.

BRIEF DESCRIPTION OF THE DRAWINGS

FIG. 1A-1B, 2, 3, 4, 5 illustrate prior art.

FIG. 8A illustrates an embodiment of the present invention having a plurality of electrode shafts extending through a common lumen.

FIGS. 8B-8C illustrate embodiments of shafts having common lumens for the passage of electrode shafts therethrough.

FIGS. 9A-9B illustrate an embodiment of a lead having a shaft having a distal end split into at least two finger portions.

FIGS. 10A-10B illustrate an alternative embodiment of a lead having a shaft having a distal end split into at least two finger portions.

FIG. 10C illustrates a lead of the present invention including a sheath having an angled distal end.

FIG. 10D illustrates a lead of the present invention including a sheath having a cutout.

DETAILED DESCRIPTION OF THE INVENTION

Figure 2:
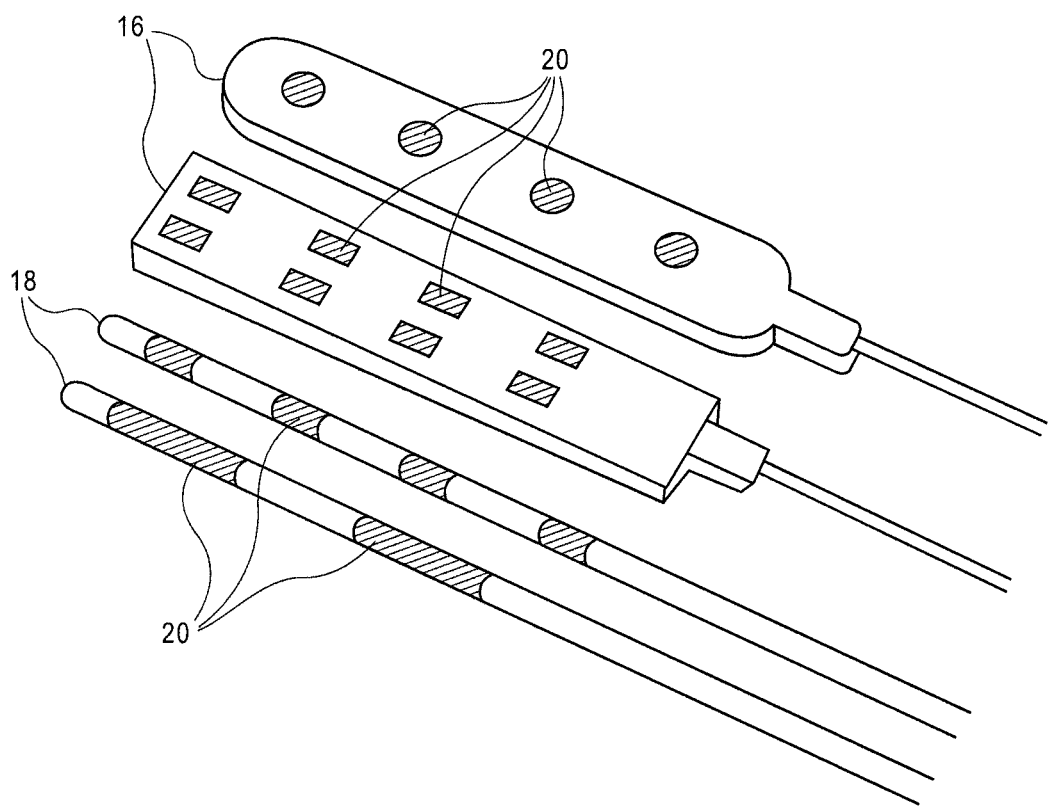
Figure 3:
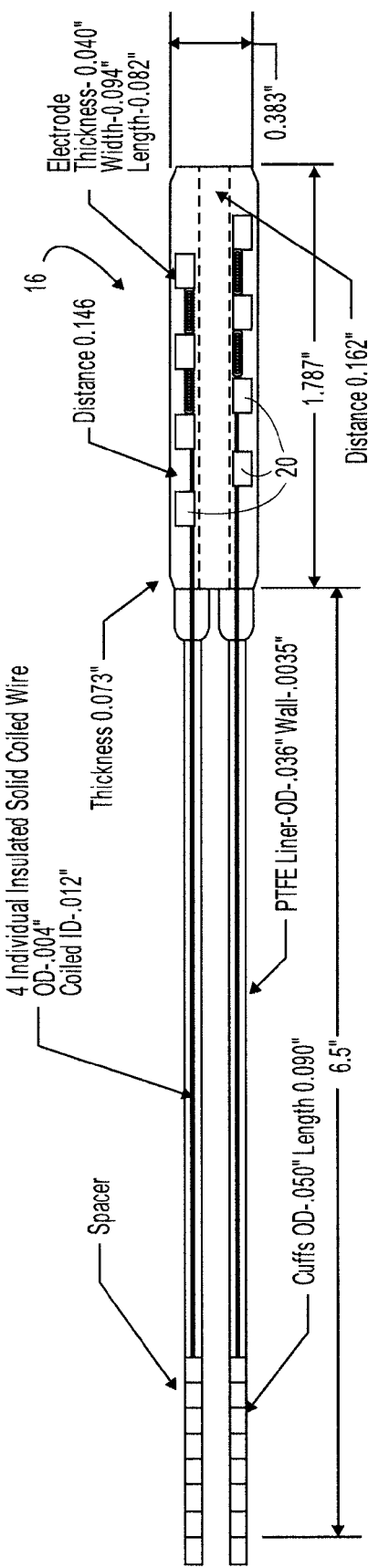
Figure 4:
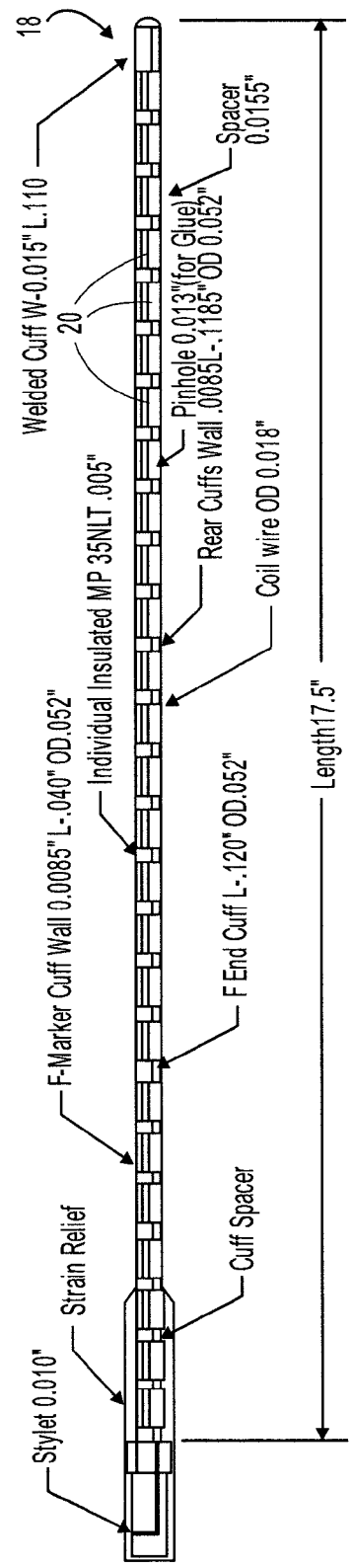
Figure 5:
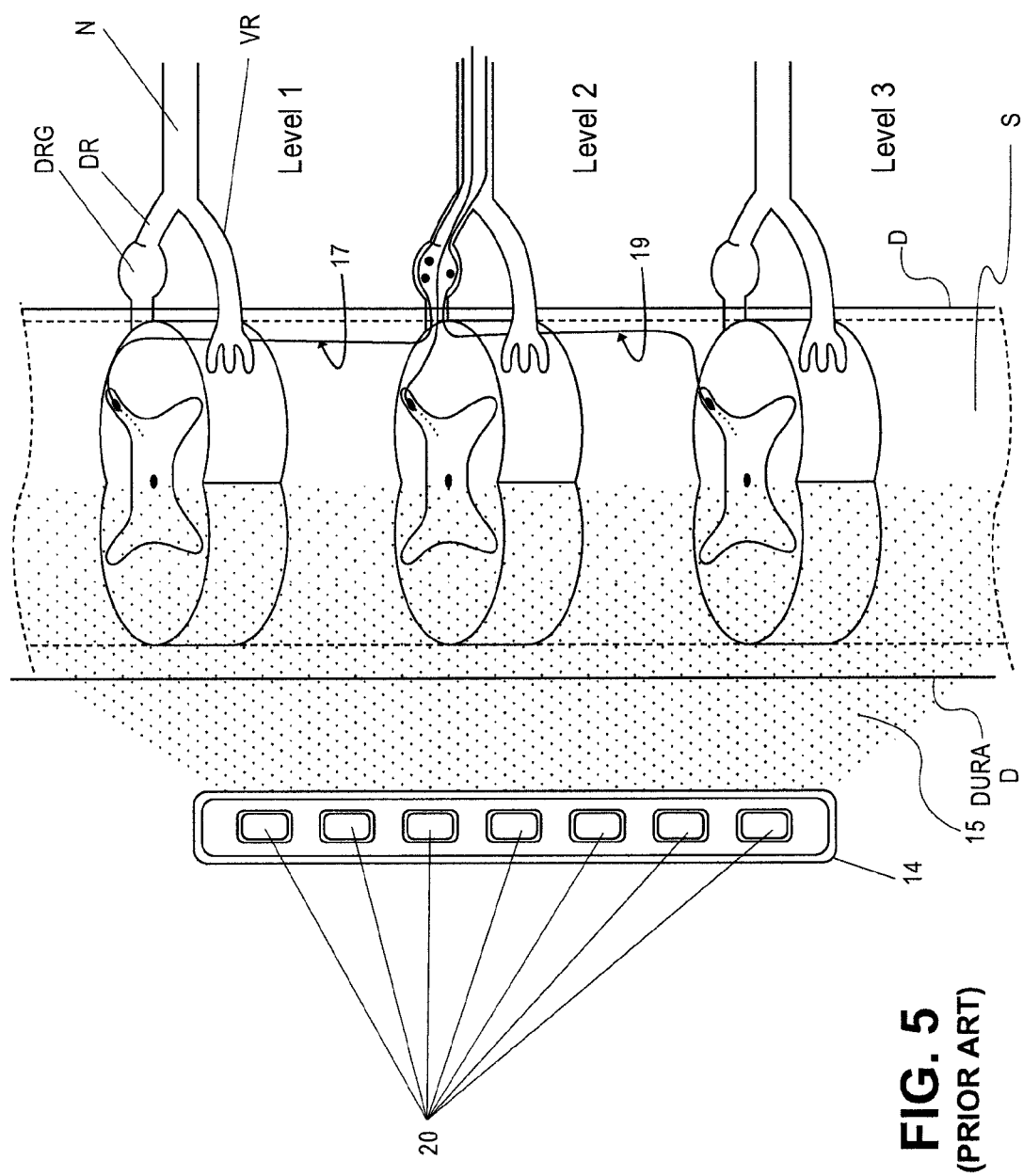
Figure 6A:
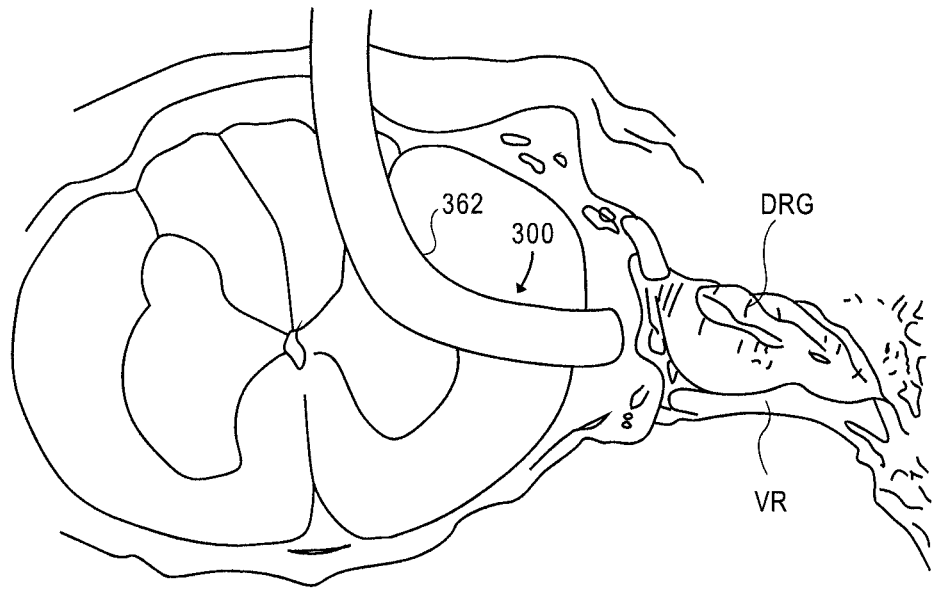
FIGS. 6A-6B illustrate a lead of the present invention having a shaft and a plurality of electrode shafts, each having at least one electrode, wherein the lead is positioned near the DRG.
Figure 6B:
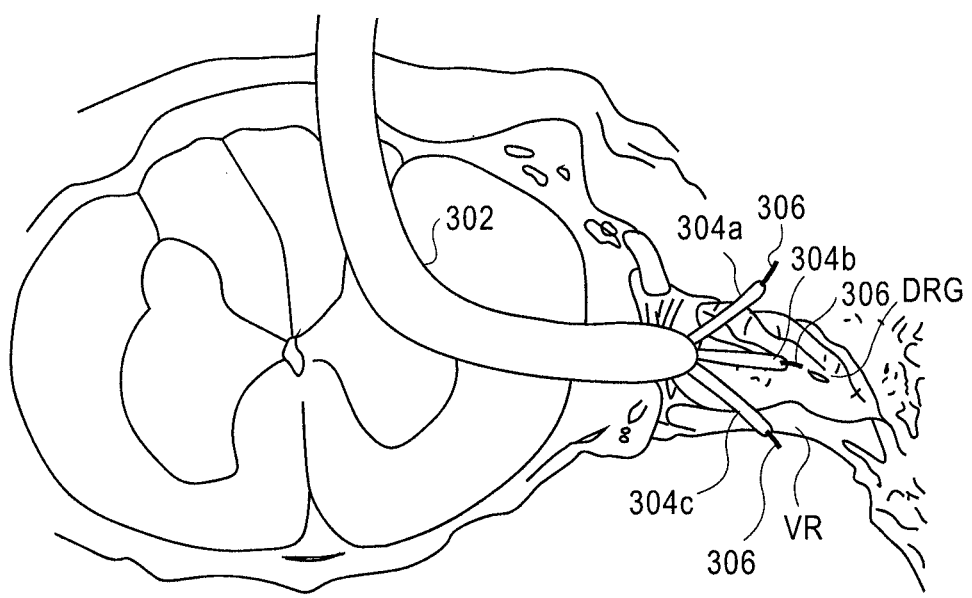

As mentioned previously, the examples provided herein illustrate the dorsal root ganglion (DRG) as the target tissue, however it may be appreciated that the present invention may be used to stimulate any target tissue within the spinal anatomy or general anatomy. In some instances the target tissue may be adjacent to or in very close proximity to other tissue of which stimulation is to be avoided or reduced. For example, FIGS. 6A-6B provide a histological cross-sectional illustration of spinal anatomy in which the DRG (target tissue) is adjacent to the ventral root VR (non-targeted tissue). A lead 300 of the present invention is shown accessing the DRG via a retrograde spinal column approach. The lead 300 has a shaft 302 and a plurality of electrode shafts 304a, 304b, 304c, each having at least one electrode 306 (typically positioned near its tip), which are extendable from the shaft 302. As shown in FIG. 6A, the lead 300 is typically advanced toward the target tissue with the electrode shafts 304a, 304b, 304c retracted therein. Once the shaft 302 is desirably positioned, the electrode shafts 304a, 304b, 304c are extended, as illustrated in FIG. 6B.

In the extended or expanded position, the electrodes 306 are positioned in disperse locations within a specific target area (e.g. in, on, around or near the DRG). The position of the electrodes 306 may be adjusted, independently or together, such as by advancement or retraction of the electrode shafts 304. In some embodiments, the electrode shafts 304 are precurved so that their tips disperse, expanding radially outwardly, as illustrated. Optionally, the electrode shafts 304 may be steerable.

In the example of FIG. 6B, although the plurality of electrode shafts 304a, 304b, 304c extend from the shaft 302, only the electrode 306 of electrode shaft 304b actually contacts the target tissue, the DRG. The electrode 306 of electrode shaft 304a falls outside of the DRG and the electrode 306 of electrode shaft 304c contacts the ventral root VR. In this instance, stimulation energy may be applied to the electrode 306 of the electrode shaft 304b and not to the electrode 306 of the electrode shaft 304c. This would provide specific stimulation to the DRG (so as to manage pain) while minimizing any stimulation to the ventral root VR (so as to avoid a motor response). Likewise, stimulation energy may not be applied to electrode 306 of electrode shaft 304a so as to conserve energy. Such a stimulation pattern may be particularly useful in embodiments wherein the electrode shafts move together. In embodiments wherein the electrode shafts move independently, electrode shaft 304a and electrode shaft 304c may be removed.

Thus, stimulation may be applied to the target area by supplying electrical energy to all of the electrodes 306 or to a subset of the electrodes 306. In this manner, an area of tissue surrounding the disperse electrodes 306 may be stimulated. In many instances, the location of the electrode shafts 304 and/or electrodes 306 upon delivery are not visible to the practitioner. Thus, the practitioner is unaware as to which electrodes 306 are disposed closest to the target tissue. In such instances, electrical energy may be supplied to the electrodes 306 individually or in groups until the desired effect is achieved. For example, the patient's pain level may be evaluated by stimulation via each of the electrodes 306 individually or in groups, and only the electrodes 306 which provide the desired response will be used for stimulation. These are likely but not necessarily the one or more electrodes 306 which are positioned closest to the DRG.

It may be appreciated that the shaft 302 is advanced toward the DRG by any suitable approach. Embodiments of these approaches may include passing through, near or along one or more posterior or lateral openings in the bony structure of the spinal column. An example of a posterior opening is an opening between adjacent spinous processes. An example of a lateral opening is the foramen or opening at least partially defined by the articulating processes and the vertebrae. In particular, the shaft 302 may be advanced by a retrograde, antegrade or lateral approach to the dorsal root and DRG from the spinal column, such as a translaminar approach. Alternatively, the shaft 302 may be advanced by a retrograde, antegrade or lateral approach to the dorsal root and DRG from outside of the spinal column, such as from a side or traditional percutaneous approach or a transforamenal approach. In further examples, the shaft 32 may be advanced to the dorsal root and DRG via an antegrade or retrograde approach between an articulating process and the vertebral body. The leads of the present invention may also be positioned by any other suitable method or approach.

Figure 7A:
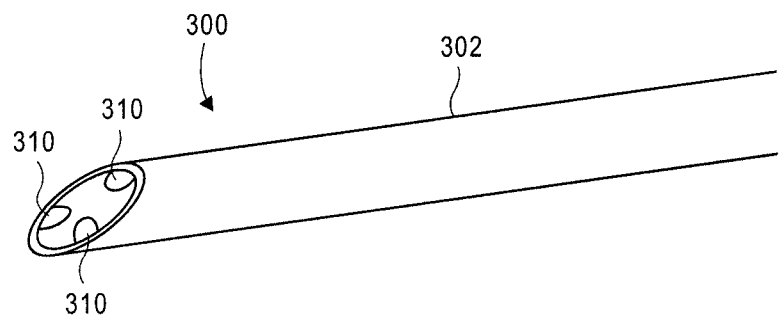
FIGS. 7A-7B illustrate an embodiment of a lead of the present invention having three advanceable electrode shafts.
Figure 7B:
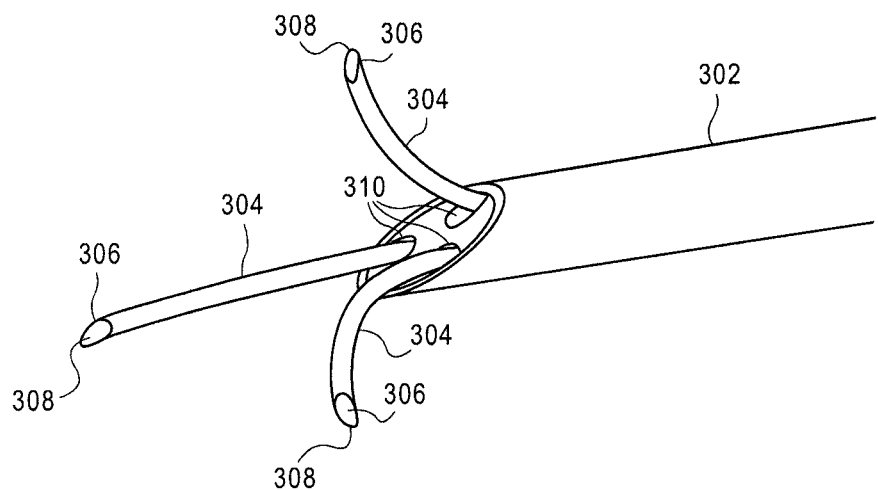

FIGS. 7A-7B illustrate an example embodiment of a lead 300 of the present invention. In this embodiment, the lead 300 comprises a shaft 302 having a plurality of internal lumens 310. In this example, three lumens 310 are depicted, however more or less lumens 310 may be present, such as one, two, four, five, six or more lumens 310. In this embodiment, an electrode shaft 304 is extendable through each of the lumens 310, as illustrated in FIG. 7B. In this embodiment, an electrode 306 is disposed near each tip 308 and each electrode 306 is electrically connected to a conductive wire (not shown) which extends along the length of the shaft 302 and connects with a remotely implanted IPG. In this embodiment, the electrode shafts 304 are precurved so that the tips 308 disperse, expanding radially outwardly as shown, during advancement of the electrode shafts 304 through the lumens 310. It may be appreciated that the electrode shafts may extend in various directions, including 15, 30, 45, 90, 120, 180 degrees apart, to name a few. It may also be appreciated that the shafts 304 may alternatively curve inwardly or in any other desired pattern.

The electrode shafts 304 may be comprised of any suitable material, including a polymer, memory metal or spring metal, to name a few. Alternatively or in addition, the electrode shafts 304 may be steerable. Likewise, one or more of the electrode shafts 304 may be independently positionable and/or steerable. Further, one or more the electrode shafts 304 may be independently advanceable and retractable. Once the position of the electrode shafts 304 are optionally adjusted and desirably placed, the shafts 304 may be fixed in place in relation to the shaft 302 and optionally each other.

FIG. 8A illustrates another embodiment of a lead 300 of the present invention. The lead 300 comprises a shaft 302 and a plurality of electrode shafts 304 extending therefrom. The shaft 302 may have a variety of configurations, including a large central lumen 312, as illustrated in FIG. 8B. The electrode shafts 304 pass through the central lumen 312 and extend therefrom. FIG. 8C illustrates an alternative embodiment wherein the shaft 302 comprises a ring lumen 314 surrounding an axial lumen 316. The electrode shafts 304 pass through the ring lumen 314 and extend therefrom. This allows other tools or devices to be passed through the axial lumen 316. Thus, in each of these embodiments the electrode shafts 304 extend through a common lumen.

Referring back to FIG. 8A, twelve electrode shafts 304 are shown, however more or less shafts 304 may extend therethrough depending on the size of the shaft 302 and lumens. An electrode 306 is disposed near each tip 308 of the electrode shafts 304. In this embodiment, the electrode shafts 304 are precurved so that as the electrode shafts 304 advance, shafts 304 expand radially outwardly dispersing the tips 308. Alternatively, the shaft 302 may be retracted, exposing the electrode shafts 304 and allowing the unrestrained shafts 304 to expand radially outwardly. In this embodiment, the plurality of electrode shafts 304 extend in a circular configuration radially outwardly from the shaft 302. Again, once the position of the electrode shafts 304 are optionally adjusted and desirably placed, the electrode shafts 304 may be fixed in place in relation to the shaft 302 and optionally each other.

FIGS. 9A-9B illustrate another embodiment of a lead 300 of the present invention. In this embodiment, the lead 300 has a shaft 302 comprising a split distal end 320. Here, shaft 302 is comprised of a flexible material (such as a flexible polymer or metal), and the distal end 320 is cut so as to create at least two finger portions 322. Thus, the shaft 302 includes a central lumen 326 which may be used for advancement of tools or devices, such as a stylet, therethrough. An electrode 306 is positioned near the tip of each finger portion 322. In this embodiment, the electrodes 306 are disposed on an outside surface of the finger portions 322. However the electrodes 306 may alternatively be positioned on an inside surface or along a distal cross-section. It may be appreciated that more than one electrode may be disposed on each finger portion 322, such as an electrode array. Each electrode 306 is electrically connected with a conductive wire 324 which extends along the shaft 302 and connects with an IPG to provide electrical signals to the associated electrode.

FIG. 9A illustrates the finger portions 322 aligned with a longitudinal axis 323. FIG. 9B illustrates the finger portions 322 expanded radially outwardly from the longitudinal axis 323 so that the electrodes 306 are dispersed. Such expansion may be achieved by a variety of features. For example, each finger portion 322 may be precurved radially outwardly. Such precurvature may be achieved by heat-setting of a polymer or embedding a shape-memory wire or ribbon into each finger portion 322. The finger portions 322 are capable of being held in a restrained position by an outer sheath. Retraction of the outer sheath releases the finger portions 322 and allows the precurvature to draw the finger portions 322 radially outwardly by recoil.

Alternatively, each finger portion 322 may include a pull-wire, wherein applying tension to the pull-wires draws the finger portions 322 radially outwardly. In some embodiments, the position of the finger portions 322 may be adjusted independently by applying tension to the pull-wires independently.

FIGS. 10A-10D illustrate another embodiment of a lead 300 having a shaft 302 comprising a split distal end 320 creating at least two finger portions 322. In this embodiment, the shaft 302 is formed from a nitinol tube covered by an insulated braided wire. In this embodiment, the finger portions 322 have sharp tips upon which the electrodes 306 are plated. Each electrode 306 is electrically connected with a conductive wire 324 which extends along the shaft 302 and connects with an IPG to provide electrical signals to the associated electrode. FIG. 10B illustrates the finger portions 322 expanded radially outwardly so that the electrodes 306 are dispersed. Such expansion is achieved due to shape memory of the nitinol tube. As shown, the shaft 302 includes a central lumen 326 which may be used for advancement of tools or devices, such as a stylet, therethrough.

Typically, the finger portions 322 would be covered with a sheath 330 that is removable to allow expansion of the finger portions 322. Optionally, the sheath 330 may be angled, as illustrated in FIG. 10C, to allow preferential expansion. As shown, the angled sheath 330 covers some of the finger portions 322, holding them in a restrained, unexpanded state, while revealing some of the finger portions 322, allowing them to expand radially outwardly. The proportion of expansion depends on the angle of the sheath 330 and on the radius of curvature of the finger portions 322.

Additionally or alternatively, multiple sheaths may be used with cutouts for each finger portion 322 to allow even more preferential expansion options. For example, FIG. 10D illustrates an embodiment having a first sheath 330a and a second sheath 330b. The first sheath 330a has a tube shape and is capable of restraining all of the finger portions 322 when positioned over the finger portions 332. The second sheath 330b has a cutout 332 near its distal end. When the first sheath 330a is retracted, as shown in FIG. 10D, restraint of the finger portions 322 is maintained by the second sheath 330b in all areas except in the area of the cutout 332 which allows the revealed finger portion 332' to expand radially outwardly. The second sheath 330b may be rotated to reveal any desired finger portions (s). It may be appreciated that the sheaths 330a, 330b are coaxial and may be layered in any order. It may also be appreciated that the sheaths 330 of FIGS. 10C-10D may be used with any leads 300 of the present invention.

In some embodiments, the leads of the present invention are passable through a 16 gauge needle, 17 gauge needle, 18 gauge needle or a smaller needle. However, in some embodiments, such leads may be passable through a 14-15 gauge needle or a larger needle. In some embodiments, the electrode(s) of the present invention have a less than 2 mm square area, or in some embodiments an approximately 0.6-1 mm square area.

In embodiments having reduced dimensions in electrode area and overall size (e.g. outer diameter), such reductions are possible due to increased specificity of the stimulation energy. By positioning at least one of the electrodes on, near or about the dorsal root ganglion, the stimulation energy is supplied directly to the target anatomy (i.e. the DRG). Thus, a lower power may be used than with a leads which is positioned at a greater distance from the target anatomy. For example, the peak power output of the leads of the present invention are typically in the range of approximately 20 μW-0.5 mW. Such reduction in power requirement for the leads of the present invention in turn may eliminate the need to recharge the power source in the implanted pulse generator (IPG). Moreover, the proximity to the stimulation site also reduce the total amount of energy required to produce an action potential, thus decreasing the time-averaged power significantly and extending battery life.

The above described leads of the present invention may be used with or without the assistance of visualization during the implantation procedure. However, in instances wherein visualization is desired, some embodiments of the lead include means for delivering contrast agent to the target tissue area to assist in visualization via fluoroscopy or other imaging methods. For example, in the embodiment illustrated in FIGS. 7A-7B, the shaft 302 may include an additional lumen through which contrast agent is injected. Or, the electrode shafts 304 may be sized so as to allow simultaneous passage of contrast agent through one or more of the lumens 310. Or, the electrode shafts 304 may include a lumen for passage of contrast agent therethrough. The different types of tissue, such a muscle and nerve, may provide contrast differences that may assist in positioning the lead in a desired location.

Any of the above described devices and systems may be adapted for delivery of a drug or therapeutic agent to a desired target tissue site. Rather than electrodes, hollow tubes may be used. The tubes may be positioned in dispersed locations with a specific target area. Some or all of the tubes may be used to deliver the therapeutic agent to the desired tissue. Or the one or more tubes that fall near the target tissue may be used to delivery the therapeutic agent to the tissue while the other tubes are not used.

Although the foregoing invention has been described in some detail by way of illustration and example, for purposes of clarity of understanding, it will be obvious that various alternatives, modifications and equivalents may be used and the above description should not be taken as limiting in scope of the invention.

What is claimed is:

1. A method of stimulating only a dorsal root ganglion comprising:
   advancing a shaft having a distal end into an epidural space;
   bending the shaft so that the distal end is curved laterally away from a midline of a spinal cord and toward an intervertebral foramen containing the dorsal root ganglion;
   extending at least two electrode shafts from the distal end of the shaft into the intervertebral foramen towards the dorsal root ganglion, wherein each electrode shaft has an electrode;
   positioning each electrode within the intervertebral foramen in proximity to the dorsal root ganglion; and
   energizing at least one of the electrodes to stimulate only the dorsal root ganglion without eliciting a motor response in ventral root in closest proximity to the dorsal root ganglion.

2. A method as in claim 1, wherein energizing includes energizing a minimum number of electrodes to stimulate only the dorsal root ganglion and not energizing remaining electrodes.

3. A method as in claim 1, wherein energizing includes energizing at least one electrode positioned near the dorsal root ganglion and not energizing at least one other electrode positioned further way from the dorsal root ganglion.

4. A method as in claim 1, wherein extending includes extending at least one of the electrode shafts radially outwardly from the shaft.

5. A method as in claim 1, wherein extending includes extending the at least two electrode shafts in directions at least 45 degrees apart.

6. A method as in claim 5, wherein extending includes extending the at least two electrode shafts in directions at least 90 degrees apart.

7. A method as in claim 1, wherein extending includes extending a plurality of electrode shafts in a circular configuration radially outwardly from the shaft.

8. A method as in claim 1, wherein extending includes extending the at least two electrode shafts through separate lumens in the shaft.

9. A method as in claim 1, wherein extending includes extending at least some of the at least two electrode shafts through a common lumen in the shaft.

10. A method as in claim 1, wherein advancing includes advancing the shaft at least partially through a foramen.

11. A method as in claim 1, wherein positioning includes steering each electrode shaft.

12. A method as in claim 1, wherein positioning includes independently positioning each electrode shaft.

* * * * *